United States Patent
Dealwis

(10) Patent No.: US 8,512,677 B2
(45) Date of Patent: Aug. 20, 2013

(54) PYRO-GLUTAMATE Aβ TARGETING AGENTS

(75) Inventor: Chris Dealwis, Highland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/266,545

(22) PCT Filed: Apr. 27, 2010

(86) PCT No.: PCT/US2010/032570
§ 371 (c)(1),
(2), (4) Date: Oct. 27, 2011

(87) PCT Pub. No.: WO2010/129276
PCT Pub. Date: Nov. 11, 2010

(65) Prior Publication Data
US 2012/0045392 A1    Feb. 23, 2012

Related U.S. Application Data

(60) Provisional application No. 61/172,812, filed on Apr. 27, 2009.

(51) Int. Cl.
*A61K 49/00* (2006.01)
*A61K 49/16* (2006.01)
*G01N 33/53* (2006.01)
*A61B 5/055* (2006.01)

(52) U.S. Cl.
USPC ............ 424/9.1; 424/9.3; 424/9.341; 435/7.1

(58) Field of Classification Search
None
See application file for complete search history.

(56) References Cited

U.S. PATENT DOCUMENTS 7,122,374 B1 * 10/2006 Saido et al. .................. 435/331
2004/0223912 A1 * 11/2004 Montalto et al. ............. 424/1.49
2009/0035295 A1   2/2009 Hillen et al.

FOREIGN PATENT DOCUMENTS

WO   WO 2005018424 A2 *  3/2005
WO   WO 2008-156622 A1    12/2008

OTHER PUBLICATIONS

Padlan EA et al. (1989) Structure of an antibody-antigen complex: crystal structure of the HyHEL-10 Fab-lysozyme complex. Proc Natl Acad Sci USA, 86:5938-5942.*
Paul WE, editor. Fundamental Immunology, Third Edition. Raven Press, New York, 1993, pp. 292-295.*
Saido TC et al. (1995) Dominant and differential deposition of distinct beta-amyloid peptide species, AbetaN3(pE), in senile plaques. Neuron, 14:457-466.*
Villemagne VL et al. (Aug. 2008) The ART of loss: Abeta imaging in the evaluation of Alzheimer's disease and other dementias. Mol. Neurobiol. 38:1-15.*
Guntert, A., et al., "High Sensitivity analysis of amyloid-beta peptide composition in amyloid deposits from human and PS2APP mouse brain", Neuroscience, 2006, vol. 143, pp. 461-475.
Vivian, Hook, et al., "Alternative Pathways for Production of Beta-Amyloid Peptides of Alzheimer's Disease", Bio. Chem., Aug. 2008, vol. 389, No. 8, pp. 993-1006.

* cited by examiner

*Primary Examiner* — Elizabeth C Kemmerer
*Assistant Examiner* — Kimberly A Ballard
(74) *Attorney, Agent, or Firm* — Tarolli, Sundheim, Covell & Tummino LLP

(57) ABSTRACT

A method of inhibiting amyloid beta aggregation in a mammal includes administering an amount of a pyro-Glu-(3-40/42)-Aβ targeting agent and/or fragment thereof that specifically binds to an epitope of the N terminus end of a pyro-Glu-(3-40/42)-Aβ effective to inhibit amyloid beta aggregation in the subject.

15 Claims, 3 Drawing Sheets

Fibrillation assay of pyroglu in presence and absence of monoclonal antibody (PGA5)

14 month old Borchelt (APPswe/PS1dE9 PGA5 antibody 1:100 (red) Nuclear dappy staining (Blue))

PYRO-GLUTAMATE Aβ TARGETING AGENTS

RELATED APPLICATION

This application corres. to PCT/US2010/032570, filed Apr. 27, 2010, which claims priority from U.S. Provisional Application No. 61/172,812, filed Apr. 27, 2009, the subject matter which is incorporated herein by reference in its entirety.

TECHNICAL FIELD

The present invention relates to agents specific to pyro-glutamate amyloid beta and to use of such agents to detect and to inhibit amyloid beta aggregation in a subject.

BACKGROUND

Soluble proteins and peptides can sometimes aggregate into insoluble, self-assembled filamentous aggregates including amyloid and amyloid-like structures. Current interest in amyloid fibrils and related aggregates arises from their involvement in diseases, such as Alzheimer's disease (AD), type 2 diabetes, prion diseases, and other protein misfolding disorders (Dobson, C. M. (2002) Getting out of shape, Nature 418, 729-730). Although the precursor molecule used for forming the fibril associated with each disease is different, they for the most part appear to share very similar assembly progressions and similar structural details in the aggregated forms. Data from genetic, animal models and biochemical studies suggest that amyloid beta (Aβ) plays a central role in the pathology of AD. The abnormal excessive accumulation of especially toxic versions of the Aβ peptide in the brain is a common characteristic of AD. The Aβ molecule is a 40 to 42 amino acid proteolytic product of the amyloid precursor protein (APP) resulting from the sequential cleavage by two membrane-bound aspartic proteases called the β and γ secretases, respectively (Haass, C., Koo, E. H., Mellon, A., Hung, A. Y., and Selkoe, D. J. (1992) Targeting of cell-surface beta-amyloid precursor protein to lysosomes: alternative processing into amyloid-bearing fragments, Nature 357, 500-503). Although the Aβ40 is more abundant in the blood and CSF, Aβ42 is thought to be the more toxic species (Selkoe, D. J. (1997) Alzheimer's disease: genotypes, phenotypes, and treatments, Science 275, 630-631). As Aβ is a natural product that is present in the brains and the cerebrospinal fluid (CSF) of normal human beings, its mere presence cannot be responsible for causing AD (Haas et al.; Seubert, P., Vigo-Pelfrey, C., Esch, F., Lee, M., Dovey, H., Davis, D., Sinha, S., Schlossmacher, M., Whaley, J., Swindlehurst, C., and et al. (1992) Isolation and quantification of soluble Alzheimer's beta-peptide from biological fluids, Nature 359, 325-327; Vigo-Pelfrey, C., Lee, D., Keim, P., Lieberburg, I., and Schenk, D. B. (1993) Characterization of beta-amyloid peptide from human cerebrospinal fluid, J Neurochem 61, 1965-1968; Walsh, D. M., Tseng, B. P., Rydel, R. E., Podlisny, M. B., and Selkoe, D. J. (2000) The oligomerization of amyloid beta-protein begins intracellularly in cells derived from human brain, Biochemistry 39, 10831-10839). Instead, it is the self-assembly of Aβ that is responsible for neuronal injury. Both amyloid beta-based plaques and neurofibrillary tangles are found in AD postmortem brains. Neurofibrillary tangles are composed mainly of abnormally phosphorylated tau protein (a neuron-specific phosphoprotein that is the major constituent of neuronal microtubules). However, recent evidence show that it is the toxic forms of Aβ that might be responsible for the pathology of Alzheimer's.

SUMMARY

The present invention relates to pyro-Glu-(3-40)-Aβ and pyro-Glu-(3-42)-Aβ (together referred to as pyro-Glu-(3-40/42)) targeting agents and to therapeutic, diagnostic, and detection methods, which employ such agents.

In one aspect of the present invention, the pyro-Glu-(3-40/42)-Aα targeting agents can specifically target an N-terminal epitope of pyro-Glu-(3-40/42)-Aα. The pyro-Glu-(3-40/42)-Aβ targeting agent can also include an agent, which does not specifically bind to wild-type amyloid beta. The pyro-Glu-(3-40/42)-Aβ targeting agent can be an antibody or a fragment thereof.

A further aspect of the invention relates to a method of generating an anti-pyro-Glu-(3-40/42)-Aβ antibody. The method includes administering to a mammal an effective amount of the pyro-Glu-(3-40/42)-Aβ form of amyloid beta or fragment thereof that causes the mammal to produce antibodies against pyro-Glu-(3-40/42)-Aβ. The method can also include administering an adjuvant to the mammal in conjunction with the pyro-Glu-(3-40/42)-Aβ or fragment thereof. In some aspects, the mammal can be a mouse, a rat, or a rabbit.

Another aspect of the present invention relates to a molecular probe that includes a pyro-Glu-(3-40/42)-Aβ targeting agent, which specifically targets an N-terminal epitope of pyro-Glu-(3-40/42)-Aβ. The molecular probe also includes a detectable moiety which can be directly or indirectly linked to the pyro-Glu-(3-40/42)-Aβ targeting agent.

Another aspect of the present invention relates to a method of detecting pyro-Glu-(3-40/42)-Aβ in a subject's brain. The method includes administering to the subject's brain a molecular probe. The molecular probe includes a pyro-Glu-(3-40/42)-Aβ targeting agent that specifically targets an N-terminal epitope of pyro-Glu-(3-40/42)-Aβ. The molecular probe also includes a detectable moiety which can be directly or indirectly linked to the pyro-Glu-(3-40/42)-Aβ targeting agent. The method further includes the step of visualizing the molecular probe with an in vivo imaging modality.

Yet another aspect of the present invention relates to a method of diagnosing a neurodegenerative disorder in a subject. The method includes administering to the subject's brain a molecular probe. The molecular probe includes a pyro-Glu-(3-40/42)-Aβ targeting agent that specifically targets an N-terminal epitope of pyro-Glu-(3-40/42)-Aβ. The molecular probe also includes a detectable moiety which can be directly or indirectly linked to the pyro-Glu-(3-40/42)-Aβ targeting agent. The method further includes the step of visualizing the molecular probe with an in vivo imaging modality. The method also includes the step of correlating the presence of the molecular probe in the subject's brain with the subject having a neurodegenerative disorder.

The neurodegenerative disorder can be Alzheimer's disease or an early stage of Alzheimer's disease. The neurodegenerative disorder can also be Mild Cognitive Impairment (MCI).

Yet another aspect of the present invention relates to a method of quantifying the pyro-Glu-(3-40/42)-Aβ load in a subject's brain. The method includes administering to the subject's brain a molecular probe. The molecular probe includes a pyro-Glu-(3-40/42)-Aβ targeting agent that specifically targets an N-terminal epitope of pyro-Glu-(3-40/42)-Aβ. The molecular probe also includes a detectable moiety which can be directly or indirectly linked to the pyro-Glu-(3-40/42)-Aβ targeting agent. The method further includes the step of visualizing the molecular probe with an in vivo imaging modality. The method also includes the step of correlating a distribution of the molecular probe in the subject's brain with the amount of pyro-Glu-(3-40/42)-Aβ in the subject's brain.

Another aspect of the present invention relates to a method of inhibiting pyro-Glu-(3-40/42)-Aβ aggregation in a subject's brain. The method includes the step of administering to the subject's brain a therapeutically effective amount a pyro-Glu-(3-40/42)-Aβ targeting agent in order to inhibit the formation of pyro-Glu-(3-40/42)-Aβ aggregates in the subject's brain. The pyro-Glu-(3-40/42)-Aβ targeting agent includes a pyro-Glu-(3-40/42)-Aβ targeting agent that specifically targets an N-terminal epitope of pyro-Glu-(3-40/42)-Aβ. The pyro-Glu-(3-40/42)-Aβ targeting agent can be administered intravenously. The pyro-Glu-(3-40/42)-Aβ targeting agent can be an antibody or binding fragment thereof.

The present invention also relates to a method of treating Alzheimer's in a subject. The method includes the step of administering a therapeutically effective amount of pyro-Glu-(3-40/42)-Aβ targeting agent to the subject's brain. The pyro-Glu-(3-40/42)-Aβ targeting agent includes a pyro-Glu-(3-40/42)-Aβ targeting agent that specifically targets an N-terminal epitope of pyro-Glu-(3-40/42)-Aβ. The pyro-Glu-(3-40/42)-Aβ agent can be an antibody or binding fragment thereof. The pyro-Glu-(3-40/42)-Aβ targeting agent can also be a monoclonal antibody.

Further features and advantages of the present invention will become apparent from the ensuing detailed description, considered together with the appended figure.

DETAILED DESCRIPTION

Figure 1:
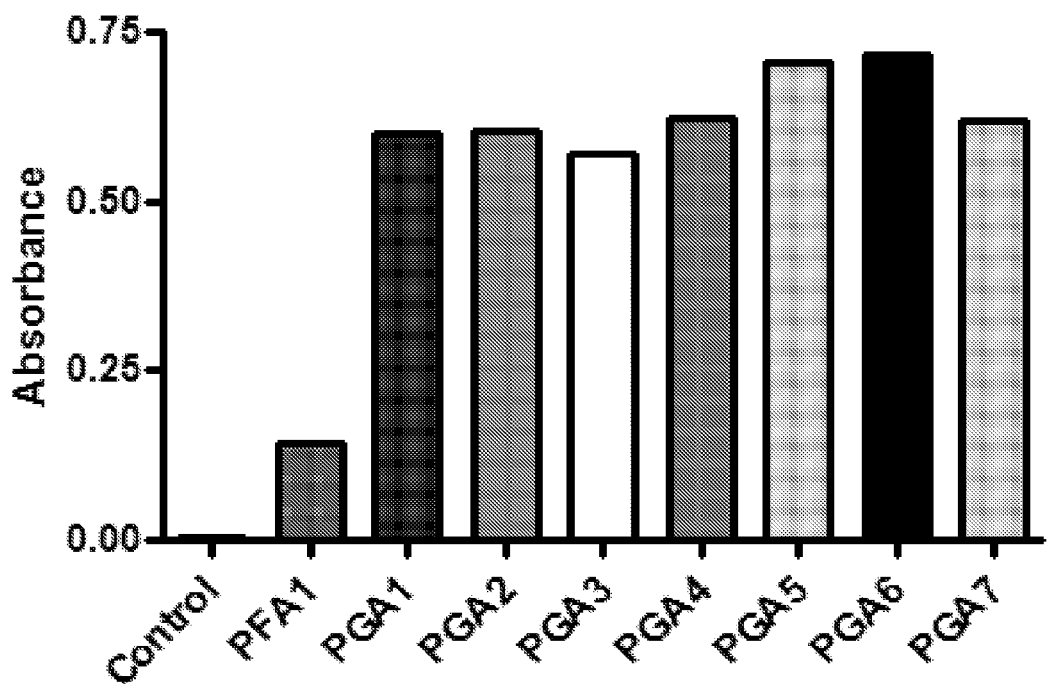
FIG. 1 is a graph illustrating an initial ELISA of pyro-glu-antibodies (PGA). PFA1 was a positive control that is known to bind the pyro-Glu-Phe-Arg-His-Asp-Ser (SEQ ID NO: 3) epitope with micromolar affinity. The data shows that the PGA1-6 binds with much higher affinity compared to PFA1.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

The term "polypeptide" is used herein as a generic term to refer to native protein, fragments, or analogs of a polypeptide sequence. Hence, native protein, fragments, and analogs are species of the polypeptide genus.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "monoclonal" refers to an antibody that specifically binds to a sequence of amino acid and/or a specific epitope of an antigen. For example, PGA5 is a monoclonal antibody that is specific only to the N-terminal amino acid sequence of Pyro-Glu(3-40/42)-Aβ. Because the antibody is monoclonal, it would recognize a domain/motif that contains the sequence contained in SEQ ID NO: 2.

The term "polyclonal" refers to antibodies that recognizes multiple epitope sites on a single antigen. For example, a polyclonal antibodies against pyro-Glu(3-40/42)-Aβ indicates that the antibody will bind several sites of the pyro-Glu (3-40/42)-Aβ protein.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The terms "oligomer" and "polymer" are used interchangeable. The terms "oligomer" and "polymer" refer to the association of more than one monomer of a specific protein, peptide, or peptide fragments. The terms "oligomer" and "polymer" in this invention specifically relates to the ability of pyro-Glu(3-40/42)-Aβ protein monomers to form protein aggregates with itself or with other proteins.

The term "agent" is used herein to denote a chemical compound, a mixture of chemical compounds, a biological macromolecule, or an extract made from biological materials.

The terms "patient", "subject", "mammalian host," and the like are used interchangeably herein, and refer to mammals, including human and veterinary subjects.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "a disease or disorder associated with the aggregation of pyro-Glu(3-40/42) Aβ," as used herein, refers to a disease or disorder caused, directly or indirectly, by the aggregation of pyro-Glu(3-40/42) Aβ, a disease or disorder that is mediated, directly or indirectly, by the aggregation of pyro-Glu(3-40/42) Aβ, or a product generated by the aggregation of pyro-Glu(3-40/42) Aβ. The term also refers to a disease or disorder that is exacerbated the aggregation of pyro-Glu(3-40/42) Aβ, or a product generated by the aggregation of pyro-Glu(3-40/42) Aβ.

The present invention relates to agents that are specific to and/or bind pyro-glutamate amyloid beta and to use of such agents to detect and to inhibit amyloid beta (Aβ) aggregation in a subject. Animal model studies have shown that amyloid beta plays a central role in the pathology of Alzheimer's disease (AD). It was found that N-terminally modified pyro-glutamate Aβ (pyro-Glu(3-40/42)-Aβ) (SEQ ID NO: 2) are a cytotoxic species of wild-type Aβ (e.g., SEQ ID NO: 1) that is responsible for early events in AD pathology. Analysis of AD senile plaques shows that the major component is N-terminally modified Aβ beginning with a pyro-Glu(3-40/42)-Aβ that results from post-translational modification. In some cases, pyro-Glu(3-40/42)-Aβ and pyro-Glu(11-40)-Aβ constitute more than 50% of the Aβ in neuritic plaques. Short peptides (pyro-Glu(3-40/42)-Aβ and pyro-Glu(11-40)-Aβ) are observed prior to the formation of amyloid plaques and neurofibrillary tangles, but disappear after the onset of AD, evidence that they play a role in the pathology of the disease.

It was found that the addition of pyro-Glu-(3-40/42)-Aβ can cause wild type Aβ to form aggregates 250-fold faster than it would on its own, perhaps acting as a seed for oligomer and fibril formation during the early stages of the disease. Pyro-Glu-(3-40/42)-Aβ allows Aβ to form fibrils even though its critical concentration for fibril formation is much higher (1 μm) than its pM concentration in the brain. Thus, agents that target pyro-Glu-(3-40/42)-Aβ can be used to substantially inhibit aberrant Aβ aggregation, to treat neurodegenerative disorders associated with aberrant Aβ aggregation (e.g., Alzheimer's disease), and in the early detection of neurodegenerative disorders associated with aberrant Aβ aggregation, such as Alzheimer's.

One aspect of the present invention therefore relates to a method of inhibiting pyro-Glu-(3-40/42)-Aβ aggregates in a subject's brain. The method includes administering to the subject a therapeutically effective amount of a pyro-Glu-(3-40/42)-Aβ targeting agent (e.g., an anti-pyro-Glu-(3-40/42)-Aβ antibody). The pyro-Glu-(3-40/42)-Aβ targeting agents can be used in therapeutic methods for the treatment of diseases mediated, directly or indirectly, by pyro-Glu-(3-40/42/42)-Aβ aggregation (e.g., Alzheimer's disease and cognitive impairment).

In one embodiment, the pyro-Glu-(3-40/42)-Aβ targeting agent can be used in a method of treating an amyloidgenic disease. The term "amyloidgenic disease" includes any disease associated with (or caused by) the formation or deposition of insoluble amyloid fibrils. Exemplary amyloidgenic disease include, but are not limited to Alzheimer's disease (AD), mild cognitive impairment, Parkinson's Disease with dementia, Down's Syndrome, Diffuse Lewy Body (DLB) disease, Cerebral Amyloid Angiopathy (CAA), vascular dementia and mixed dementia (vascular dementia and AD). Different amyloidgenic diseases are defined or characterized by the nature of the polypeptide component of the fibrils deposited. For example, in subjects or patients having Alzheimer's disease, amyloid beta protein (e.g., wild-type, variant, or truncated amyloid beta protein) is the characterizing polypeptide component of the amyloid deposit.

The method includes administering to the subject a therapeutically effective amount of pyro-Glu-(3-40/42)-Aβ targeting agent. A "therapeutically effective amount" of a pyro-Glu-(3-40/42)-Aβ targeting agent is an amount that is effective to inhibit the aggregation of amyloid beta by at least about 10%, at least about 20%, at least about 30%, at least about 40%, at least about 50%, at least about 60%, at least about 70%, at least about 80%, at least about 90%, or more.

The pyro-Glu-(3-40/42)-Aβ targeting agents of the present invention can be directed to or specifically bind to an N-terminal epitope of pyro-Glu-(3-40/42)-Aβ, which act as a seed in propagating amyloid beta fibril formation. Therefore, the pyro-Glu-(3-40/42)-Aβ targeting agents of the present invention can inhibit amyloid beta fibril formation as well as inhibit amyloid beta aggregation and the onset of amyloidgenic disease.

An aggregated amyloid protein is meant to include fully or partially aggregated pyro-Glu-(3-40/42)-Aβ proteins. By partially aggregated pyro-Glu-(3-40/42)-Aβ proteins, it is meant that aggregation of additional wild type or pyro-Glu-(3-40/42)-Aβ proteins onto existing aggregated wild-type or pyro-Glu-(3-40/42)-Aβ proteins, e.g., protofibrils or fibrils, can occur under the appropriate conditions. In certain embodiments, the aggregated amyloid proteins are Alzheimer's disease associated beta amyloid fibrils. In certain embodiments, the aggregated amyloid proteins are protofibrils, type-1 fibrils, type-2 fibrils, neuritic plaque, diffuse amyloid, or combinations thereof. By inhibit of aggregation, it is meant, e.g., that the amyloid proteins are unable to properly interact with each other to effect, e.g., formation of, or growth of, aggregates of amyloid proteins, e.g., the growth of protofibrils, the conversion of protofibrils into fibrils, the growth of fibrils and the growth of neuritic plaque Inhibiting interaction is also meant to include reversing aggregation of the pyro-Glu-(3-40/42)-Aβ proteins.

The pyro-Glu-(3-40/42)-Aβ specific targeting agent can be any agent that binds to an N-terminal epitope of pyro-Glu-(3-40/42)-Aβ and inhibits aggregation of pyro-Glu-(3-40/42)-Aβ and Aβ. In certain embodiments of the present invention, the agent can be an antibody, (poly)peptide, nucleic acid, small organic compound, ligand, hormone, peptide nucleic acid, peptidomimetic, which binds to a N-terminal region epitope of pyro-Glu-(3-40/42)-Aβ.

In one aspect of the invention, the targeting agent can comprise an antibody that specifically targets and/or binds to the toxic pyro-Glu(3-40/42) Aβ monomer and fibrils, which contain pyro-Glu(3-40/42) Aβ. Antibodies contemplated by the present invention can specifically target N-terminal epitopes of pyro-Glu(3-40/42) amyloid beta. In one example, antibodies of the present invention can target an epitopes corresponding to or defined by SEQ ID NO: 3 (pyr-EFRHDS) of pyro-Glu(3-40/42) Aβ. Antibodies can also target epitopes corresponding to SEQ ID NO: 4 (pyr-EFRHDSG), SEQ ID NO:5 (pyr-EFRHDSGY), SEQ ID NO: 6(pyr-EFRHDSGYE), SEQ ID NO: 7(pyr-EFRHDSGYEV), SEQ ID NO: 8 (pyr-EFRHDSGYEVH), SEQ ID NO: 9 (pyr-EFRHDSGYEVHH), SEQ ID NO: 10 (pyr-EFRHDSGYEVHHQ), SEQ ID NO: 11(pyr-EFRHDSGYEVHHQK) and SEQ ID NO: 12 (pyr-EFRHDSGY EVHHQKL).

Antibodies specific to pyro-Glu-(3-40/42)-Aβ can be prepared using standard methods well known in the art. For the production of antibodies, various host animals, including but not limited to rabbits, mice, rats, etc., may be immunized by injection with a peptide corresponding to the N-terminal region of the pyro-Glu-(3-8)-Aβ (e.g., SEQ ID NO: 3 (pyr-EFRHDS), SEQ ID NO: 4 (pyr-EFRHDSG), SEQ ID NO:5 (pyr-EFRHDSGY), SEQ ID NO: 6(pyr-EFRHDSGYE), SEQ ID NO: 7(pyr-EFRHDSGYEV), SEQ ID NO: 8 (pyr-EFRHDSGYEVH), SEQ ID NO: 9 (pyr-EFRHDSGYEVHH), SEQ ID NO: 10 (pyr-EFRHDSGYEVHHQ), SEQ ID NO: 11(pyr-EFRHDSGYEVHHQK) and SEQ ID NO: 12 (pyr-EFRHDSGY EVHHQKL)). The peptide may be attached to a carrier, such as BSA, by means of a side chain functional group or linkers attached to a side chain functional group. Various adjuvants may be used to increase the immunological response, depending on the host species, including but not limited to keyhole limpet hemocyanin, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as BCG (bacilli Calmette-Guerin) and *Corynebacterium parvum*.

In another aspect of the invention, the pyro-Glu-(3-40/42)-Aβ specific targeting agents can be an antibody that specifically binds to pyro-Glu-(3-40/42)-Aβ (i.e., anti-pyro-Glu-(3-40/42)-Aβ antibody) but not the wild-type Aβ(1-40).

An example of a pyro-Glu(3-40/42) Aβ antibody in accordance with the present invention that specifically binds to SEQ ID NO: 3 was isolated and characterized as described in the Examples. The Examples of the present application disclose a pyro-Glu(3-40/42) Aβ antibody identified as PGA5 that is produced by the hybridoma cell line deposited under ATCC Accession Number PTA-11009. PGA5 specifically binds to SEQ ID NO: 3 of pyro-Glu-(3-40/42)-Aβ but not the wild-type Aβ(1-40). The PGA5 antibody was prepared by injection of a mouse with a peptide corresponding to the N-terminal region of the pyro-Glu-(3-8)-Aβ (e.g., SEQ ID NO: 3 (pyr-EFRHDS)) that was coupled to KLH via terminal extension (e.g., pyr-EFRHDS-GGC-KLH)

In another embodiment, the heavy chain variable coding regions and the light chain variable coding regions of PGA5 were determined. The $V_H$ amino acid sequence of PGA5 is shown in SEQ ID NO: 13. The $V_L$ amino acid sequence of PGA5 is shown in SEQ ID NO: 14. Accordingly, one aspect of the invention relate to an isolated monoclonal antibody, or antigen binding portion thereof comprising: (a) a heavy chain variable region comprising the amino acid sequence of SEQ ID NO: 13; and/or (b) a light chain variable region comprising the amino acid sequence of SEQ ID NO: 14; wherein the antibody specifically binds to pyro-Glu(3-40/42) Aβ.

Another aspect of the invention, relates to antibodies that comprise the heavy chain and light chain CDR1s, CDR2s and CDR3s of PGA5, or combinations thereof. Accordingly, in another aspect, the invention provides an isolated monoclonal antibody, or antigen binding portion thereof comprising: (a) a heavy chain variable region comprising CDR1, CDR2, and CDR3; and/or (b) a light chain variable region comprising CDR1, CDR2, and CDR3; wherein the antibody specifically binds to pyro-Glu-(3-40/42)-Aβ but not the wild-type Aβ(1-40).

In another aspect, the invention relates to antibodies that bind to the same epitope on pyro-Glu-(3-40/42)-Aβ as the PGA5 (having $V_H$ and $V_L$ sequences as shown in SEQ ID NOs: 13 and 14). Such antibodies can be identified based on their ability to cross-compete with PGA5 in standard pyro-Glu-(3-40/42)-Aβ binding assays. The ability of a test antibody to inhibit the binding of PGA5 to pyro-Glu-(3-40/42)-Aβ demonstrates that the test antibody can compete with PGA5 for binding to pyro-Glu(3-40/42) Aβ and thus binds to the same epitope on pyro-Glu-(3-40/42)-Aβ as PGA5. In an aspect of the invention, the antibody that binds to the same epitope on pyro-Glu-(3-40/42)-Aβ as PGA5 is a human monoclonal antibody. Such human monoclonal antibodies can be prepared and isolated.

In yet another aspect, an antibody of the invention comprises heavy and light chain variable regions comprising amino acid sequences that are homologous to the amino acid sequences of the preferred antibodies described herein, and wherein the antibodies retain the desired functional properties of the pyro-Glu-(3-40/42)-Aβ antibodies of the invention. For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to the amino acid sequence of SEQ ID NO: 13; (b) the light chain variable region comprises an amino acid sequence that is at least 80% homologous to the amino acid sequence of SEQ ID NO: 14; and (c) the antibody specifically binds to pyro-Glu (3-40/42) Aβ.

In various aspects, the antibody can be, for example, a human antibody, a humanized antibody or a chimeric antibody. In other aspects, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 13 or 14, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., PGA5), or conservative modifications thereof, and wherein the antibodies retain the desired functional properties of the anti-pyro-Glu-(3-40/42)-Aβ antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences or conservative modifications thereof; and the antibody specifically binds to pyro-Glu-(3-40/42)-Aβ.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Accordingly, another aspect of the invention pertains to an isolated monoclonal antibody, or antigen binding portion thereof, comprising a heavy chain variable region comprising CDR1, CDR2, and CDR3 sequences of SEQ ID NO: 13, and a light chain variable region comprising CDR1, CDR2, and CDR3 sequences comprising an amino acid sequence of SEQ ID NO 14. Thus, such antibodies contain the $V_H$ and $V_L$ CDR sequences of PGA5 yet may contain different framework sequences from these antibodies.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-pyro-Glu-(3-40/42)-Aβ monoclonal antibodies, or antigen binding portions thereof, comprising a heavy chain variable region comprising: (a) $V_H$ CDR1, CDR2, and CDR3 regions comprising the amino acid sequences of SEQ ID NO: 13, or an amino acid sequence having one, two, three, four or five amino acid substitutions, deletions or additions as compared to SEQ ID NO: 13; and/or (b) $V_K$ CDR1, CDR2, and CDR3 regions comprising the amino acid sequences of SEQ ID NO: 14, or an amino acid sequence having one, two, three, four or five amino acid substitutions, deletions or additions as compared to SEQ ID NO: 14.

Preparation of Antibodies

Antibodies in accordance with the invention can be prepared in a mouse using standard methods well known in the art. The monoclonal antibody of the present invention can be converted into a humanized version for therapeutic use. The antibody can be made by contract or in house into humanized, fully human, chimeric, recombinant for therapeutic use. The hybridoma cell lines discussed herein are readily generated by those of ordinary skill in the art, given the guidance provided herein. The antibodies produced by the subject cell lines do not generate an adverse response. Adverse response is defined as an unwanted response.

Antibodies in accordance with the present invention can be expressed in cell lines other than hybridoma cell lines. Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive pyro-Glu-(3-40/42)-Aβ binding properties.

The results of the present invention indicate that antibodies can be made more efficacious than currently available antibodies against pyro-Glu-(3-40/42)-Aβ and therefore will be efficacious in treating disorders associated with and/or mediated by the alternative complement pathway.

Human antibodies against a variety of antigens can also be produced from non-human transgenic mammals comprising human immunoglobulin loci. Typically these immunoglobulin loci can encode substantially human sequence antibodies, preferably 95% or more identical to human sequences, more preferably 98-99% or more identical, and most preferably 100% identical. The immunoglobulin loci can be rearranged or unrearranged, and can comprise deletions or insertions relative to the natural human immunoglobulin loci. The loci can include genetic elements (e.g., non-coding elements such as enhancers, promoters, and switch sequences, or coding elements such as mu constant region gene segments) from other species, and from non-immunoglobulin loci, that do not contribute substantially to the coding portion of secondary repertoire (non IgM) antibodies. The human immunoglobulin loci contained in these transgenic mammals preferably include unrearranged sequences of natural human heavy and human light chain loci. Usually, the endogenous immunoglobulin locus of such transgenic mammals is functionally inactivated (U.S. Pat. No. 5,589,369, Takeda, S. et al., 1993, *EMBO J.* 12:2329-2366; Jakobovits, A., et al., 1993, *Proc. Natl. Acad. Sci. U.S.A.* 90:2551-2555; Kitamura, D. and Rajewsky, K., 1992, *Nature* 356: 154-156; Gu, H. et al., 1991, *Cell* 65:47-54; Chen, J. et al., *EMBO J.* 12:821-830; Sun, W. et al., 1994, *J. Immunol* 152:695-704; Chen, J. et al., 1993, *Intl. Immunology* 5:647-656; Zou, X. et al., 1995, *Eur. J. Immunol* 25:2154-2162; Chen, J. et al., 1993 *Intl. Immunology* 5:647-656; Boudinot, P., et al, 1995, *Eur. J. Immunol.* 25:2499-2505; Chen, J. et al., 1993, *Proc. Natl. Acad. Sci.* 90:4528-4532; Roes, J. and Rajewsky, K., 1991, *Intl. Immunology* 3:1367-1371; Gu, H. et al., 1993, *Cell* 73:1155-1164; Taki, S. et al., 1993, *Science* 262: 1268-71; Kitamura, D. et al., 1991, *Nature* 350:423-6; Lutz, C. et al., 1998, *Nature* 393:797-801; Zou, Y. et al, 1994, *Current Biology* 4: 1099-

1103; Chen, J. et al., 1993, *EMBO J.* 12:4635-4645; Serwe, M. and Sablitzky, F., 1993, *EMBO J.* 12:2321-2327; Sanchez, P. et al., 1994, *Intl. Immunology* 6:711-719; Zou, Y. et al., 1993, *EMBO J.* 12:811-820). Inactivation of endogenous immunoglobulin genes preferably can be achieved, e.g., by targeted homologous recombination. The exogenous human immunoglobulin loci can be associated the endogenous mouse chromosomes or can be of (e.g., part of, inserted within or attached to) an introduced transchromosome. Transchromosomes are introduced into a cell as a nonendogenous chromosome or chromosome fragment having a centromere and two telomeres. These transchromosomes commonly comprise telomere and centromere sequences and can comprise deletions relative to the parental intact chromosome. Transchromosomes can also comprise additional inserted sequences. A single transchromosome comprising two or three different immunoglobulin loci provides for genetic linkage of these loci which increases the fraction of transgenic offspring that are useful for making human antibodies. Preferred forms of transchromosomes are those described in detail in Tomizuka, K. et al., 2000, *Proc. Natl. Acad. Sci. U.S.A.* 97:722-727, Tomizuka, K. et al., 1997, *Nature Genetics* 16:133-143, and WO 97/07671, WO 98/37757 and WO 00/10383, each of which is incorporated by reference in its entirety for all purposes. Transchromosomes can also include integrated selectable markers and other sequences not found in the parent intact chromosome. In the event of recombination between a transchromosome and an endogenous mouse chromosome, sequences from the transchromosome are inserted or added to the endogenous mouse chromosome. Transchromosomes can be modified by deletion, translocation, substitution and the like, as described in WO 98/37757, EP 0972445 and WO 00/10383, which are incorporated herein by reference for all purposes. For example, transchromosomes can be fragmented spontaneously in the course of introduction into mouse embryonic stem (ES) cells, fragmented by telomere-directed truncation and/or translocated by Cre/loxP site-specific recombination or similar methods. Such recombination or translocation events can be promoted by specifically inserting recombination sites (e.g., loxP sequences and others; see, e.g., Abuin, A. and Bradley, A., 1996, *Mol. Cell Biol.* 16: 1851-1856; Mitani, K. et al., 1995, *Somat. Cell. Mol. Genet.* 21:221-231; Li, Z. W. et al., 1996, *Proc. Natl. Acad. Sci. U.S.A.* 93:6158-6162; Smith, A J. et al., 1995, *Nat. Genet.* 9:376-385; Trinh, K R. and Morrison, S. L., 2000, *J. Immunol. Methods* 244:185-193; Sunaga, S. et al., 1997, *Mol. Reprod Dev.* 46: 109-113; Dymecki, S. M., 1996, *Proc. Natl. Acad Sci. U.S.A.* 93:6191-6196; Zou, Y R. et al., 1994, *Curr. Biol.* 4: 1099-1103; Rudolph, U. et al., 1993, *Transgenic Res.* 2:345-355; Rickert, R. C. et al., 1997, *Nucleic Acids Res.* 25:1317-1318). In the case of introduced loxP sites, expression of a transgene encoding the cre recombinase will promote recombination between the two loxP sites. Transchromosomes can also be a fusion chromosome consisting of different chromosome fragments as a result of the translocation described above. Transchromosomes can be autonomous. Autonomous transchromosomes are distinct from, are noncontiguous with, and are not inserted into the endogenous mouse chromosomes. These autonomous transchromosomes comprise telomere and centromere sequences that enable autonomous replication. Alternatively, transchromosome sequences can be translocated to mouse chromosomes after introduction into mouse cell nuclei. The endogenous mouse chromosomes include 19 autosomal chromosome pairs and the X and Y chromosomes.

Introduction of exogenous human immunoglobulin loci can be achieved by a variety of methods including, for example, microinjection of half-day embryo pronuclei, transfection of embryonic stem cells, or fusion of embryonic stem cells with yeast spheroplasts or micronuclei comprising transchromosomes. The transgenic mammals resulting from the processes described above are capable of functionally rearranging the introduced exogenous immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO 93/12227 (1993); U.S. Pat. Nos. 5,877,397, 5,874,299, 5,814, 318, 5,789,650, 5,770,429, 5,661,016, 5,633,425, 5,625,126, 5,569,825, 5,545,806, *Nature* 48:1547-1553 (1994), *Nature Biotechnology* 14, 826 (1996), Kucherlapati, WO 91/10741 (1991), WO 94/02602 (1993), WO 96/34096 (1995), WO 96/33735 (1996), WO 98/24893 (1997), U.S. Pat. Nos. 5,939, 598, 6,075,181, 6,114,598, Tomizuka, K. et al., 2000, *Proc. Natl. Acad. Sci. U.S.A.* 97:722-727, Tomizuka, K. et al., 1997, *Nature Genetics* 16:133-143, and Tomizuka, K., WO 97/07671, WO 98/37757, WO 00/10383, and JP 2000-42074 (each of which is incorporated by reference in its entirety for all purposes). Transgenic nonhuman mammals such as rodents are particularly suitable. Monoclonal antibodies can be prepared, e.g., by fusing B-cells from such mammals to suitable immortal cell lines using conventional Kohler-Milstein technology. Monoclonal antibodies can also be accessed directly from individual B cells, isolated from the medium, using PCR amplification of V regions (Schrader et al., 1997, U.S. Pat. No. 5,627,052). Alternatively, FACs sorted, or otherwise enriched B cell preparations can be used as a source of RNA or DNA for PCR amplification of V region sequences. Phage display methods (described below) can also be used to obtain human antibody sequences from immunized transgenic mice comprising human immunoglobulin loci. The human antibody V region sequences obtained by these methods can then be used to generate intact antibodies that retain the binding characteristics of the original parent antibodies. This process is described below.

A further approach for obtaining human antibodies is to screen a cDNA library from cells according to the general protocol outlined by Huse et al., 1989, *Science* 246:1275-1281. Such cells can be obtained from a human immunized with the desired antigen, fragments, longer polypeptides containing the antigen or fragments or anti-idiotypic antibodies. The cells can also be obtained from transgenic non-human animals expressing human immunoglobulin sequences. The transgenic non-human animals can be immunized with an antigen or collection of antigens. The animals can also be unimmunized. The V region encoding segments of the cDNA sequences are then cloned into a DNA vector that directs expression of the antibody V regions. Typically, the V region sequences are specifically amplified by PCR prior to cloning. Also typically, the V region sequences are cloned into a site within the DNA vector that is constructed so that the V region is expressed as a fusion protein. The collection of cloned V region sequences is then used to generate an expression library of antibody V regions. To generate an expression library, the DNA vector comprising the cloned V region sequences is used to transform eukaryotic or prokaryotic host cells. In addition to V regions, the vector can optionally encode all or part of a viral genome, and can comprise viral packaging sequences. In some cases, the vector does not comprise an entire virus genome, and the vector is then used together with a helper virus or helper virus DNA sequences. The expressed antibody V regions are found in, or on the surface of, transformed cells or virus particles from the transformed cells. This expression library, comprising the cells or virus particles, is then used to identify V region sequences that encode antibodies, or antibody fragments reactive with predetermined antigens. To identify these V region sequences, the expression library is screened or selected for reactivity of the expressed V regions with the predetermined antigens. The cells or virus particles comprising the cloned V region sequences, and having the expressed V regions, are screened or selected by a method that identifies or enriches for cells or virus particles that have V regions reactive (e.g., binding association or catalytic activity) with a predetermined antigen. For example, radioactive or fluorescent labeled antigen that then binds to expressed V regions can be detected and used to identify or sort cells or virus particles. Antigen bound to a solid matrix or bead can also be used to select cells or virus particles having reactive V regions on the surface. The V region sequences thus identified from the expression library can then be used to direct expression, in a transformed host cell, of an antibody or fragment thereof, having reactivity with the predetermined antigen. The protocol described by Huse is rendered more efficient in combination with phage-display technology. See, e.g., Dower et al., WO 91/17271 and McCafferty et al., WO 92/01047, U.S. Pat. Nos. 5,871,907, 5,858,657, 5,837,242, 5,733,743, and 5,565,332, (each of which is incorporated by reference in its entirety for all purposes). In these methods, libraries of phage are produced in which members (display packages) display different antibodies on their outer surfaces. Antibodies are usually displayed as Fv or Fab fragments. Phage displaying antibodies with a desired specificity can be selected by affinity enrichment to the antigen or fragment thereof. Phage display combined with immunized transgenic non-human animals expressing human immunoglobulin genes can be used to obtain antigen specific antibodies even when the immune response to the antigen is weak.

In a variation of the phage-display method, human antibodies having the binding specificity of a selected murine antibody can be produced. See, for example, Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for the selected are selected. Artificial antibodies that are similar to human antibodies can be obtained from phage display libraries that incorporate random or synthetic sequences, for example, in CDR regions.

The heavy and light chain variable regions of chimeric, humanized, or human antibodies can be linked to at least a portion of a human constant region by various well-known methods (see, e.g., Queen et al., 1989, *Proc. Natl. Acad. Sci. U.S.A.* 86:10029-10033 and WO 90/07861; these references and references cited therein are herein incorporated by reference for all purposes). The choice of constant region depends, in part, whether antibody-dependent complement and/or cellular mediated toxicity is desired. For example, isotypes $IgG_1$ and $IgG_3$ usually have greater complement binding activity than isotypes $IgG_2$ or $IgG_4$. Choice of isotype can also affect passage of antibody into the brain. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

For some applications, non-IgG antibodies can be useful. For example, where multivalent antibody complexes are desired, IgM and IgA antibodies can be used.

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, FROM GENES TO CLONES, (VCH Publishers, New York, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., 1986, *Immunol. Rev.* 89:49), and necessary processing information sites, such as ribosome binding sites, RNA splice sites, polyadenylation sites, and transcriptional terminator sequences.

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Examples of transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

One example of a method of preparing a recombinant polyclonal antibody is by making polyclonal antibody libraries (PCAL), for instance as disclosed in U.S. Pat. No. 5,789,208 (to J. Sharon) which is hereby incorporated by reference in its entirety.

More specifically, the polyclonal antibody included in the pharmaceutical composition may be prepared by immunizing an animal, preferably a mammal, with an antigen of choice followed by the isolation of antibody-producing B-lymphocytes from blood, bone marrow, lymph nodes, or spleen. Alternatively, antibody-producing cells may be isolated from an animal and exposed to an antigen in vitro against which antibodies are to be raised. The antibody-producing cells may then be cultured to obtain a population of antibody-producing cells, optionally after fusion to an immortalized cell line such as a myeloma.

A combinatorial library may be prepared from immunized B lymphocytes by associating $V_L$ and $V_H$ randomly in a cloning vector. Thus, the recombinant polyclonal antibody is generated under such conditions that the immunoglobulin heavy chain variable region and light chain variable region gene segments are linked together randomly in order to allow for the bulk transfer of variable region light chain and heavy chain gene pairs from one vector to another, while allowing stable pairing of specific immunoglobulin variable region light chain and heavy chain gene segments as they are present upon selection from a parental library of immunoglobulin variable region light chain and heavy chain gene segment pairs encoding antibody molecules capable of reacting with or binding to an allergen.

Single cell PCR may be used in an attempt to retain the native pairing of $V_L$ and $V_H$ in the single cell. In this case antibody-producing B-lymphocytes which have been isolated from animals or humans may be fixed with a fixative solution or a solution containing a chemical such as formaldehyde, glutaraldehyde or the like. The cells are then permeabilized with a permeabilization solution comprising for example a detergent such as Brij, Tween, polysorbate, Triton X-100, or the like. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ mRNA into the corresponding cDNA sequences.

Upon reverse transcription, the resulting cDNA sequences may be amplified by PCR using primers specific for immunoglobulin genes and, in particular, for the terminal regions of the $V_H$ and $V_L$ nucleic acids. PCR procedures may be followed as disclosed in, e.g., U.S. Pat. No. 4,683,195. Preferably, the cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The amplified sequences are linked by hybridization of complementary terminal sequences. After linking, sequences may be recovered from cells. For example, after linking, cells can be washed in a solution of sodium dodecyl sulfate (SDS). The SDS precipitates out of the cells after incubation on ice and the supernatant can be electrophoresed into an agarose or acrylamide gel. Alternatively, or in combination with the SDS process, using a reagent such as digoxigenin-linked nucleotides, DNA products synthesized will remain within the cell and be amplified. The linked product is recovered upon electrophoresis of the supernatant.

After electrophoresis of the supernatant, the gel slice corresponding to the appropriate molecular weight of the linked product is removed and the DNA isolated on, for example, silica beads. The recovered DNA can be PCR amplified using terminal primers, if necessary, and cloned into vectors which may be plasmids, phages, cosmids, phagemids, viral vectors or combinations thereof. Convenient restriction enzyme sites may be incorporated into the hybridized sequences to facilitate cloning. These vectors may also be saved as a library of linked variable regions for later use.

The linked $V_H$ and $V_L$ region genes may be PCR amplified a second time using terminal nested primers, yielding a population of DNA fragments, which encode the linked $V_H$ and $V_L$ genetic regions. The grouping of $V_H$ and $V_L$ combinations is an advantage of this process and allows for the in mass or batch transfer of all clones and all DNA fragments during this and all cloning procedures.

The recombinant polyclonal antibody may be generated under such conditions that the immunoglobulin heavy chain variable region and light chain variable region gene segments are linked together in a head-to head orientation, in order to allow for the bulk transfer of variable region light chain and heavy chain pairs from one vector to another, including from phage to vector, and including from the cell of origin to phage or vector, resulting in a stable pairing of specific immunoglobulin variable region light chain and heavy chains gene segments as they are found in the original polyclonal immune response of the animal or human individual.

It may sometimes be desirable to treat the variable region gene sequences with a mutating agent. Mutating agents create point mutations, gaps, deletions or additions in the genetic sequence which may be general or specific, or random or site directed. Useful mutating agents include ultraviolet light, gamma irradiation, chemicals such as ethidium bromide, psoralen and nucleic acid analogs, or DNA modifying enzymes such as restriction enzymes, transferases, ligases and specific and nonspecific nucleases and polymerases. Moreover, it may be feasible to use mutator strains. In particular, random mutations may be introduced in the CDRs of the $V_H$ and $V_L$ region genes by oligonucleotide directed mutagenesis. Mutations introduced into the gene sequence will ultimately increase library complexity and diversity as well as affinity for antigen which may further increase the library's usefulness in treatment. Furthermore, such mutagenesis may be used on a single $V_H$ and $V_L$ pair or on a defined group of such pairs to generate a library de novo.

Vectors are transformed into suitable host cells and the cultures amplified to expand the different populations of vectors that comprise the library. Host cells for prokaryotic vectors may be a culture of bacteria such as *Escherichia coli*. Host cells for eukaryotic vectors may be a culture of eukaryotic cells such as any mammalian, insect or yeast cell lines adapted to tissue culture. Bacterial cells are transformed with vectors by calcium chloride-heat shock or electroporation, although many other transformation procedures would also be acceptable. Eukaryotic cells are transfected with calcium phosphate precipitation or electroporation, although many other transformation procedures would also be acceptable. The DNA fragments may be cloned into prokaryotic or eukaryotic expression vectors, chimeric vectors or dual vectors. The expression vector may be a plasmid, cosmid, phage, viral vector, phagemid and combinations thereof, but is preferably a phage display vector wherein the recombinant product is expressed on the phage surface to facilitate screening and selection. Useful transcriptional and translational sites may be placed on the expression vector including RNA polymerase recognition regions such as a TATA box site, a CAT site, an enhancer, appropriate splicing sites, if necessary, a AT rich terminal region and a transcription initiation site. Useful sites to facilitate translation include translational start and stop sites and ribosome binding sites. Typically, some of the more useful sites for efficient eukaryotic expression, such as the SV40, CMV, HSV or baculovirus promoter/enhancer region, are derived from viruses. The resulting recombinant antibody may be of the murine class $IgG_1$, $IgG_{2a}$, $IgG_{2b}$, IgM, IgA, IgD or IgE, the human classes $IgG_1$, $IgG_2$, $IgG_3$, $IgG_4$, IgM, $IgA_1$, $IgA_2$, IgD or IgE, or combinations or fragments thereof. Preferably, the chimeric antibody library is composed of primarily IgG antibodies or Fab antibody fragments.

The pyro-Glu-(3-40/42)-Aβ targeting agents used in the practice of a method of the invention may be formulated into pharmaceutical compositions comprising a carrier suitable for the desired delivery method. Carriers can include any material which, when combined with the pyro-Glu-(3-40/42)-Aβ targeting agent retains the high-affinity binding of the pyro-Glu-(3-40/42)-Aβ targeting agent and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

By way of example, anti-pyro-Glu-(3-40/42)-Aβ antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that can be used for a pH within this range include acetate (e.g., sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the pyro-Glu-(3-40/42)-Aβ targeting agent, may be included in the formulation. Exemplary tonicity agents include polyols, such as mannitol, sucrose or trehalose. Preferably, the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated pyro-Glu-(3-40/42)-Aβ targeting agent and/or minimize the formation of particulates in the formulation and/or reduce adsorption. Exemplary surfactants include nonionic surfactants such as polysorbates (e.g., polysorbate 20, or polysorbate 80) or poloxamers (e.g., poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e., antibody, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the pyro-Glu-(3-40/42)-Aβ targeting agent are prepared for storage by mixing the pyro-Glu-(3-40/42)-Aβ targeting agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine; histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or nonionic surfactants such as TWEEN, PLURONICS or polyethylene glycol (PEG).

In one embodiment, a formulation of the claimed invention contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and di-saccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may also be prepared. Examples of sustained-release preparations include semipermeable matrices of solid hydrophobic polymers containing the pyro-Glu-(3-40/42)-Aβ targeting agent, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The pyro-Glu-(3-40/42)-Aβ targeting agent can be administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the specific pyro-Glu-(3-40/42)-Aβ targeting agent or antibody is suitably administered by pulse infusion, particularly with declining doses of the specific pyro-Glu-(3-40/42)-Aβ targeting agent or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g., through a catheter placed close to the desired site. Most preferably, the specific binding agent or antibody of the invention is administered intravenously in a physiological solution at a dose ranging between 0.01 mg/kg to 100 mg/kg at a frequency ranging from daily to weekly to monthly (e.g., every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

A variety of approaches are known in the art to effect administration of compounds to the brain. For example, a compound may be administered by direct intraventricular or intrathecal injection, preferably via slow infusion to minimize impact on brain parenchyma. The desired drug may also be delivered using a slow release implant in the brain, or (where the drug is a polypeptide) implanted recombinant cells that produce the drug. The blood brain barrier (BBB) may be permeabilized concomitant with drug administration, to permit movement of the drug across the BBB. Permeabilizing agents include osmotic agents, such as hypertonic mannitol, or another permeabilizing agent such as bradykinin, an alkylglycerol, ultrasound, electromagnetic radiation or parasympathetic innervation.

Alternatively, receptor-mediated transport may be utilized to administer drug to the brain. It is known in the art that peptides and proteins that directly cross the BBB may serve as carriers for selective therapeutic agents that allow the therapeutic agents to cross the BBB after delivery into the bloodstream (Pan et al., Brain Research Reviews, 46:32-43, 2004; Misra et al., J. Pharm. Pharmaceut. Sci., 6:252-273, 2003; Begley, Pharmacol Ther. 2004 October; 104(1):29-45; Poduslo, US App. Pub. No. 2003/0082191; Poduslo et al., Biochem., 43:6064-6075, 2004). For example, Poduslo, WO 03/020212 describes conjugation of antibodies to amyloid-beta protein fragments which are then taken up by low-density lipoprotein receptor related protein-1, a transporter at the BBB. Other examples of peptides which cross the BBB include transferrin which binds to the transferrin receptor, a transporter at the BBB; monoclonal antibodies to the transferrin receptor such as OX26; cell penetrating peptides such as TAT transduction domain, penetratin, or Syn B1; and RAP which binds to low-density lipoprotein receptor related protein-2, another transporter at the BBB (see Pan et al., J Cell Sci. 2004 Oct. 1; 117(Pt 21):5071-8).

Receptor-mediated drug delivery to the brain may employ chimeric peptide technology, wherein a non-transportable drug is conjugated to a BBB transport vector. The latter may be a modified protein or receptor-specific monoclonal antibody that undergoes receptor-mediated transcytosis through the BBB in-vivo. Conjugation of drug to transport vector is facilitated with chemical linkers, avidin-biotin technology, polyethylene glycol linkers, or liposomes. Multiple classes of therapeutics have been delivered to the brain with the chimeric peptide technology, including peptide-based pharmaceuticals, anti-sense therapeutics including peptide nucleic acids (PNAs), and small molecules incorporated within liposomes. Alternatively, the drug may be encapsulated in a liposome or nanoparticle which is then linked to the BBB transport vector.

It will be appreciated that the pyro-Glu-(3-40/42)-Aβ targeting agent need not be formulated for delivery across the BBB when administered parenterally. In these instances, the pyro-Glu-(3-40/42)-Aβ targeting agent can be administered parenterally at an amount or dosage that is effective to reduce circulating pyro-Glu-(3-40/42)-Aβ in the subject's vasculature.

The pyro-Glu-(3-40/42)-Aβ targeting agent of the invention also may be concurrently administered with other anti-amyloidgenic therapeutic agents. Concurrent administration includes administration of the two different therapeutic agents at different times and at different routes, as long as there is some overlap in the time during which the agents are exerting their therapeutic effects.

Examples of other anti-amyloidgenic agents known in the art include other anti-amyloid-beta antibodies, anti-inflammatories known in the art (e.g., NSAIDs and Cox-2 inhibitors) that reduce the pathogenic effects of amyloid accumulation, cholesterol lowering drugs, β-secretase inhibitors, or anti-inflammatories that reduce the inflammatory response due to the administration of the pyro-Glu-(3-40/42)-Aβ targeting agent or that allow monitoring of the side effects of the pyro-Glu-(3-40/42)-Aβ targeting agent.

Another aspect of the invention relates to the use of pyro-Glu-(3-40/42)-Aβ targeting agents as molecular probes for labeling Pyro-Glu-(3-40/42)-Aβ in vivo as well as in vitro. Pyro-Glu-(3-40/42)-Aβ, which can be targeted in an animal's brain using the molecular probes of the present invention, are typically found prior to the formation of amyloid senile plaques (SPs) and neurofibrillary tangles (NFTs), but disappear after the onset of Alzheimer's disease. The molecular probes of the present can enter the brain and selectively localize to pyro-Glu-(3-40/42)-Aβ with high affinity.

For the purposes of the present invention, the molecular probes can be administered to an animal's brain tissue, where the animal's brain tissue is typically a mammal's brain tissue. The molecular probes can be administered by any method which allows the probe to interact with pyro-Glu-(3-40/42)-Aβ in the brain so as to result in labeled pyro-Glu-(3-40/42)-Aβ. These methods include, e.g., injection, infusion, deposition, implantation, or topical administration, or any other method of administration where access to the brain by the probe is obtained. Preferably, administration is by injection. Single or multiple administrations of the probe can be given. "Administered", as used herein, means provision or delivery of a molecular probe in an amount(s) and for a period of time(s) effective to label pyro-Glu-(3-40/42)-Aβ in a subject's brain.

In one aspect of the invention, the molecular probes can be used for neuroanatomical or neuropathological studies. For example, researchers studying normal brains can employ the methods described herein to examine the morphology and distribution of pyro-Glu-(3-40/42)-Aβ in an animal.

"Distribution" as used herein is the spatial property of being scattered about over an area or volume. In this case, the "the distribution of pyro-Glu-(3-40/42)-Aβ" is the spatial property of amyloid being scattered about over an area or volume included in the animal's brain tissue. One skilled in the art may use the molecular probes of the present invention to assess the pyro-Glu-(3-40/42)-Aβ distribution in a subject's brain and correlate the distribution to a specific disorder or disease state. In addition, one may also utilize the molecular probes to quantify the amyloid load in a subject as discussed below.

A molecular probe as contemplated by the present invention can include one or more pyro-Glu-(3-40/42)-Aβ targeting agents as described above and a detectable moiety. In certain embodiments, the targeting agent is directly or indirectly labeled with a detectable moiety. The role of a detectable moiety is to facilitate the detection step of a diagnostic method by allowing visualization of the complex formed by binding of the targeting agent to pyro-Glu-(3-40/42)-Aβ (or analog or fragment thereof). Preferably, the detectable moiety is selected such that it generates a signal which can be measured and whose intensity is related (preferably proportional) to the amount of the pyro-Glu-(3-40/42)-Aβ present in the sample being analyzed. Methods for labeling biological molecules such as polypeptides and antibodies are well-known in the art (see, for example, "Affinity Techniques. Enzyme Purification. Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable moieties can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

The molecular probes described herein may be used in conjunction with non-invasive neuroimaging techniques for in vivo imaging of pyro-Glu-(3-40/42)-Aβ, such as magnetic resonance spectroscopy (MRS) or imaging (MRI), or gamma imaging, such as positron emission tomography (PET) or single-photon emission computed tomography (SPECT). The term "in vivo imaging" refers to any method, which permits the detection of a labeled molecular probe, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound.

The molecular probes can also be radiolabeled with known metal radiolabels, such as Technetium-99m (99mTc). Modification of the substituents to introduce ligands that bind such metal ions can be effected without undue experimentation by one of ordinary skill in the radiolabeling art. The metal radiolabeled molecular probes can then be used to detect amyloid deposits. Preparing radiolabeled derivatives of Tc99m is well known in the art. See, for example, Zhuang et al., "Neutral and stereospecific Tc-99m complexes: [99mTc]N-benzyl-3, 4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6): 485-98, (1997).

The molecular probes of the present invention can be used to detect a neurodegenerative disorder in an subject through the use of in vivo pyro-Glu-(3-40/42)-Aβ labeling. Thus, in certain embodiments, the molecular probes described herein can be administered to a subject. The distribution of the molecular probe in the animal's brain tissue can then be visualized (e.g., with an in vivo imaging modality described above). The distribution of the molecular probe may then be correlated with the presence or absence of a neurodegenerative disorder. A distribution may be dispositive for the presence or absence of a neurodegenerative disorder or may be combined with other factors and symptoms by one skilled in the art to positively detect the presence or absence of a neurodegenerative disorder.

In one example of detecting a neurodegenerative disorder in a subject, the methods described herein can be used to compare pyro-Glu-(3-40/42)-Aβ deposits in normal brain tissues of control populations to those of a suspect animal. If the suspect animal has a neurodegenerative disorder, the pyro-Glu-(3-40/42)-Aβ load may be higher in the suspect animal compared to a control, thus possibly indicating the presence of a neurodegenerative disorder, subject to the interpretation of one skilled in the art. "Control" or "Control Population" as used herein are defined as a group of individual animals (or samples thereof) not having a neurodegenerative disorder.

More specifically, the molecular probes and methods provided of the present invention can be used to detect a pyro-Glu-(3-40/42)-Aβ related disorder in a subject through the use of in vivo pyro-Glu-(3-40/42)-Aβ labeling. A "pyro-Glu-(3-40/42)-Aβ-related disorder" refers to any pathological condition characterized by the presence of pyro-Glu-(3-40/42)-Aβ.

An example of a pyro-Glu-(3-40/42)-Aβ related disorder in which the molecular probes of the present invention can be used to detect is Alzheimer's disease. The presence of amyloid containing senile plaques and neurofibrillary tangles are known to be an important criterion of the neuropathological-histological diagnosis of neurodegenerative disorders such as Alzheimer's disease. The principal constituent of the senile plaques is Aβ. Aβ, as described above, is a peptide with an internal fragment of 39-43 amino acids of a precursor protein termed amyloid precursor protein (APP). In Alzheimer's disease, neurofibrillary tangles are generally found in the neurons of the cerebral cortex and are most common in the temporal lobe structures, such as the hippocampus and amygdala. As described above, it is also known that pyro-Glu-(3-40/42)-Aβ increases the precipitation of the plaque-forming amyloid beta peptides leading to the onset of Alzheimer's disease. Thus, the detection of pyro-Glu-(3-40/42)-Aβ in a subject's brain according to methods provided herein may be especially useful in the detection of early stages of Alzheimer's disease.

Other factors which may be measured in conjunction with the presence of pyro-Glu-(3-40/42)-Aβ in the diagnosis of Alzheimer's include dementia, atrophic brain with hydrocephalus, and other degenerative signs. These factors in combination with the occurrence of a great number of plaques allows on skilled in the art to diagnose Alzheimer's disease with high probability. The molecular probes of the present invention may be particularly useful in animal models of Alzheimer's disease (see McGowan et al. (2006) Trends in Genet. 22(5):281-289 for review of mouse models of Alzheimer's disease).

The methods included in the present invention can be used to detect other amyloidgenic disease, besides, Alzheimer's disease. Exemplary amyloidgenic disease include, but are not limited to, mild cognitive impairment, Parkinson's Disease with dementia, Down's Syndrome, Diffuse Lewy Body (DLB) disease, Cerebral Amyloid Angiopathy (CAA), vascular dementia and mixed dementia (vascular dementia and AD).

In another aspect of the present invention, the molecular probe can be used to quantify the pyro-Glu-(3-40/42)-Aβ load in a subject. The ability to track and/or quantify the pyro-Glu-(3-40/42)-Aβ load in a subject may provide a useful tool to researchers and clinicians. Pyro-Glu-(3-40/42)-Aβ load or pyro-Glu-(3-40/42)-Aβ burden, as used herein, is the amount of pyro-Glu-(3-40/42)-Aβ in a given animal or tissue sample. A reduction in pyro-Glu-(3-40/42)-Aβ load, as used herein, is the inhibition and/or dissolution of pyro-Glu-(3-40/42)-Aβ in a subject.

The methods provided can be used to monitor and compare the amyloid load in an animal prior to a given therapy, during a given therapy, or post therapeutic regimen. A reduction in a pyro-Glu-(3-40/42)-Aβ load in an animal may be indicative of the efficacy of a given therapy. This can provide a direct clinical efficacy endpoint measure of anti-pyro-Glu-(3-40/42)-Aβ therapies. For example, a subject may be administered an anti-pyro-Glu-(3-40/42)-Aβ neurodegenerative disorder therapy, such as a glutaminyl cyclase inhibitor to reduce the formation of pyro-glutamate in the subject, and the level of pyro-Glu-(3-40/42)-Aβ in the subject's brain can be measured using the therapy.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Characterization of the Pyro-Glu(3-8) Monoclonal Antibodies (mAbs)

Importance of Neutralizing Pyro-Glu-Aβ in Alzheimer's Disease

Searching for a cure or halting the progression of AD requires the identification of its etiological agent. Data from genetic, biochemical, and animal model studies suggest that Aβ plays a central role in the pathology of AD. The abnormal, excessive accumulation of especially toxic versions of the Aβ peptide in the brain is a common characteristic of AD. The Aβ molecule is a 40 to 42 amino acid proteolytic product of the amyloid precursor protein (APP) resulting from the sequential cleavage by two membrane-bound aspartic proteases called the β and γ secretases, respectively. The current consensus is that oligomers and N-terminally modified pyro-glutamate Aβ (pyro-Glu-Aβ) are cytotoxic species responsible for early events in AD pathology. Analysis of AD senile plaques shows that the major component is N-terminally modified Aβ beginning with a pyro-Glu(3-40/42)-Aβ that results from post-translational modification. In some cases, pyro-Glu(3-40/42)-Aβ and pyro-Glu(11-40)-Aβ constitute more than 50% of the Aβ in neuritic plaques. Short peptides (pyro-Glu(3-40/42)-Aβ and pyro-Glu(11-40)-Aβ) are observed prior to the formation of amyloid plaques and neurofibrillary tangles, but disappear after the onset of AD, suggesting they may play a role in the pathology of the disease. Addition of Pyro-Glu(3-40/42)-Aβ peptide caused wild-type (WT) Aβ to form aggregates 250-fold faster than it would on its own, perhaps acting as a seed for oligomer and fibril formation during the early stages of the disease. This may be why Aβ can form fibrils even though its critical concentration for fibril formation is much higher (1 µM) than its pM concentration in the brain. Pyro-Glu-Aβ peptides are more cytotoxic than WT Aβ, and inhibiting the glutaminyl cyclase responsible for forming pyro-glutamate markedly reduces plaque burden, further underscoring their importance in AD pathology. For these reasons, pyro-Glu Aβ is a good target for AD treatment.

Method of Development

We injected mice with pyro-Glu-Phe-Arg-His-Asp-Ser conjugated to KLH and collected bleeds. These sera were subjected to ELISA assays, which showed binding to pyro-Glu Aβ conjugated to ovalbumin (FIG. 1). PFA1 was used as a control. PFA1 is our earlier monoclonal antibody (mAb) raised against wild-type Aβ(1-40) protofibrils. PFA1 has low affinity for pyro-Glutamate epitope.

Classification of PGA1-7 Antibodies

Based on isotyping data only PGA 1, 5 and 7 are monoclonal antibodies (Table 1). The rest of the PGA antibodies are polyclonal antibodies. PGA 1, 5 and 7 belong to class IgG 1.

Binding and Specificity Data

We have used Surface Plasmon Resonance (SPR) and Europium Elisa Assays (EU-ELISA) to determine binding affinities of PGA1-7 to pyro-Glu(3-40/42) and Aβ(1-40) monomers and fibrils (Table 1). As the data show, the PGA (1-7) are extremely specific towards binding only pyro-Glu (3-40/42) and not wild-type Aβ(1-40). This is extremely important for treatment and diagnostic purposes of AD. As the pyro-Glu is proposed to act as a seed in propagating amyloid fibril formation which triggers the onset of AD, we want to specifically target this species. The PGA antibodies have the potential for therapeutics, diagnostics, and labeling purposes in model systems of AD.

Only PGA1, 5 and 7 are monoclonal antibodies. The rest of the PGAs are polyclonals. PGA1-6 bind pyro-Glu(3-40/42) monomers with low nM affinities but does not bind WT Aβ(1-40). PGA5 binds pyro-Glu(3-40/42) fibrils but not Aβ(1-40) fibrils.

TABLE 1

Isotyping and Surface Plasmon resonance binding data of PGA1-PGA6

| | | | KD for pyro-Glu (3-40/42) | KD for pyro-Glu (3-40/42) fibrils | KD for WT Aβ(1-40) |
|---|---|---|---|---|---|
| PGA 1 | 1F2 1F3 | IgG1 | 3.45E-8 (34.5 nM)* | 3.45E-8 (34.5 nM) | |
| PGA 5 | 1F2 2E3 | IgG1 | 4.17E-9 (4.2 nM) | 3.73E-8 (37.3 nM) | 4.53 nM | Does not bind |
| PGA 7 | 1F2 1A5 | IgG1 | 3.29E-8 (32.9 nM)* | 3.29E-8 (32.9 nM) | |
| PFA 1 | 2F12 2F7 | IgG2a | 300 nM | 300 nM | 1.8 nm |

Investigating the Influence of the PGA5 on the Kinetics of Fibril Formation

We have monitored the kinetics of fibril formation using Thioflavin (ThT) fluorescence (LeVine, H., 3rd. Thioflavine T interaction with synthetic Alzheimer's disease beta-amyloid peptides: detection of amyloid aggregation in solution. Protein Sci 2, 404-10 (1993)).

We can expect the anti-Aβ mAb to lengthen the lag phase of fibril formation as previously observed (Taylor, B. M. et al. Spontaneous aggregation and cytotoxicity of the beta-amyloid Abeta1-40: a kinetic model. J Protein Chem 22, 31-40

Figure 2:
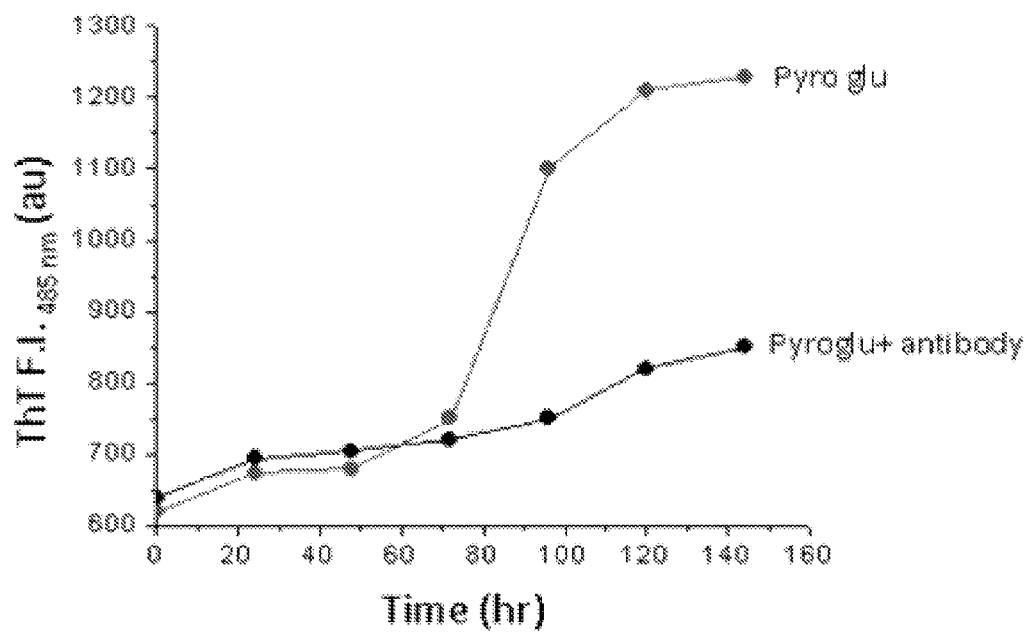
FIG. 2 is a plot showing inhibition of fibril formation by an antibody in accordance with the present invention.

(2003); Mamikonyan, G. et al. Anti-A beta 1-11 antibody binds to different beta-amyloid species, inhibits fibril formation, and disaggregates preformed fibrils but not the most toxic oligomers. J Biol Chem 282, 22376-86 (2007)). Note that the stationary phase at high ThT signal represents fibril formation, and the early lag phase is when the seeds are formed Mature fibrils treated with a small amount of antibody can undergo a significant morphology change, to an aggregate type that has low ThT signal, like conventional oligomers/protofibrils, but does not exhibit the toxicity associated with prefibrillar intermediates 3. In the assembly direction, low levels of Antibody may direct monomeric Aβ to form the non-toxic, non-fibrillar aggregates, rather than mature fibrils. We have tested our mAbs for a similar effect as show as indicated in FIG. 2. The lag phase is effected and the ThT signal becomes very low in the presence of the PGA5 antibody. The low ThT signal is associated with change of structure to a non-toxic form. Hence, these antibodies have great therapeutic potential.

We have generated monoclonal antibodies (mAbs) against the toxic pyro-Glu(3-40/42) of amyloid beta. Out of the eight PGAs generated seven have been characterized. Three called PGA 1, 5 and 7 belongs to the IgG1 class of mAbs. PGA(1-6) are highly specific against pyro-Glu(3-40/42) monomers and fibrils, but not against Aβ(1-40), making these a very unique family of mAbs that solely targets the toxic pyro-Glu amyloid beta. Fibril inhibition studies show that these mAbs lengthen the lag phase and change the structure of amyloid fibrils to a non-toxic species. The data suggest that the PGA Mabs have great therapeutic, diagnostic and labeling potential.

EXAMPLE 2

Immunostaining of Pyro-Glu(3-40/42) Fibrils in Brain Tissue

Figure 3:
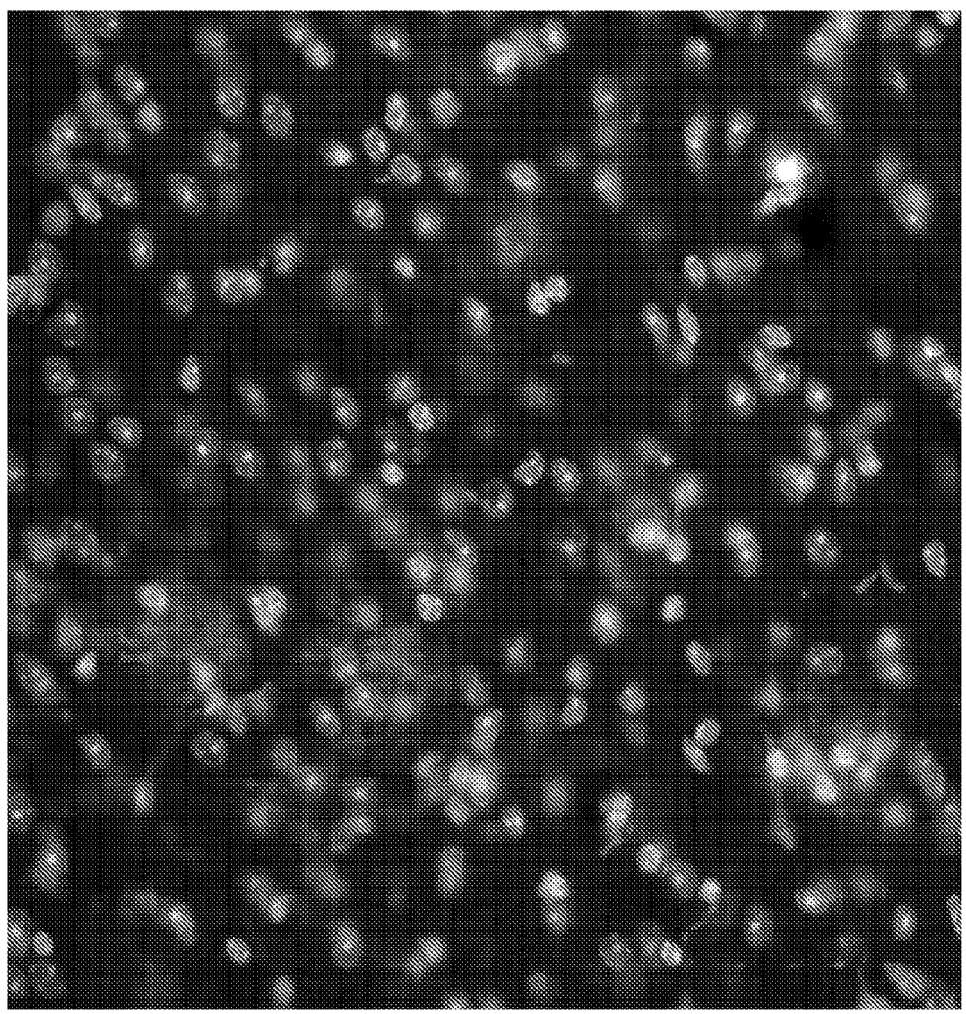
FIG. 3 is an image showing pyro-Glu-(3-40/42)-Aβ detected in brain tissue using a molecular probe comprising PGA5 antibody.

FIG. 3 illustrates an image showing mice brain tissue immunostained using a PGA5 antibody. 14 month old Borchelt (APPswe/PS1dE9 mice) brain tissue sliced 10 um thick on a cryostat in a coronal plane was used with PGA5 antibody in a 1:100 dilution. The results in FIG. 3 clearly show that the mouse brain stains well with PGA5.

The Immunohistochemistry Protocol is described below. We used the 14 month old borchelt (liced 10 um thick on a cryostat in a coronal plane.
 1. Circle sections with pap pen
 2. Rehydrate tissue section in PBS for 5 min
 3. Incubate sections in 70% formic acid for 3 min (Antigen Retrieval)
  a. Formic acid (under the hood) is 95%, dilute in water
 4. Wash with PBS 3×
 5. Quench endogenous peroxidases with 3% H2O2 in MeOH for 20 minutes
 6. Wash with PBS 3×
 7. Block with 5% normal goat serum in 0.1% Triton-X (tween) in PBS 1 hour
 8. Incubate overnight at 4 C with primary antibody in block (1:100)
 9. Wash with PBS 3×
 10. Incubate with anti mouse Alexa 546 antibody for 2 hours in block at 1:1000 (RT)
 11. Wash in PBS 3×
 12. Add DAPI 1:10,000 in PBS 1-2 minutes
 13. Wash 2× in PBS
 14. Coverslip with Prolong Gold
 15. Store in −20 C Those skilled in the art will recognize, or be able to ascertain using no more than routine experimentation, numerous equivalents to the compounds and methods of use thereof described herein. Such equivalents are considered to be within the scope of this invention and are covered by the following claims. All patents, publications, and references cited in the present application are herein incorporated by reference in their entirety.

Having described the invention, the following is claimed:

1. A method of detecting pyro-Glu-(3-40/42)-Aβ in brain tissue of a subject, the method comprising:
   administering to the subject a molecular probe that includes:
   (a) a detectable moiety, and
   (b) an antibody or binding fragment thereof that specifically binds to an N-terminal epitope of pyro-Glu-(3-40/42)-Aβ that includes SEQ ID NO: 3, wherein the antibody or binding fragment thereof comprises at least one of (i) a heavy chain variable domain that includes the amino acid sequences of the three CDRs in SEQ ID NO: 13 and a light chain variable domain that includes the amino acid sequences of the three CDRs in SEQ ID NO: 14, (ii) a heavy chain variable domain that comprises the sequence of SEQ ID NO: 13, (iii) a light chain variable domain that comprises the sequence of SEQ ID NO: 14, or (iv) a heavy chain variable domain that comprises the sequence of SEQ ID NO: 13 and a light chain variable domain that comprises the sequence of SEQ ID NO: 14; and visualizing the molecular probe with an in vivo imaging modality after administration to the subject.

2. The method of claim 1, wherein the pyro-Glu-(3-40/42) amyloid β is in the brain of a subject.

3. The method of claim 2, wherein the molecular probe is administered intravenously.

4. The method of claim 2, wherein the subject has or is at an elevated risk of Alzheimer's.

5. The method of claim 2, wherein the antibody is a monoclonal antibody.

6. A method of diagnosing a neurodegenerative disorder associated with or caused by the formation or deposition of insoluble amyloid-beta (Aβ) fibrils in a subject, comprising:
administering to the subject a molecular probe that includes:
(a) a detectable moiety, and
(b) an antibody or binding fragment thereof that specifically binds to an N-terminal epitope of pyro-Glu-(3-40/42)-Aβ that includes SEQ ID NO: 3, wherein the antibody or binding fragment thereof comprises at least one of (i) a heavy chain variable domain that includes the amino acid sequences of the three CDRs in SEQ ID NO: 13 and a light chain variable domain that includes the amino acid sequences of the three CDRs in SEQ ID NO: 14, (ii) a heavy chain variable domain that comprises the sequence of SEQ ID NO: 13, (iii) a light chain variable domain that comprises the sequence of SEQ ID NO: 14, or (iv) a heavy chain variable domain that comprises the sequence of SEQ ID NO: 13 and a light chain variable domain that comprises the sequence of SEQ ID NO: 14;
visualizing the molecular probe in the subject's brain with an in vivo imaging modality; and
correlating the presence of the molecular probe in the subject's brain with the presence of the neurodegenerative disorder, wherein an increased presence of the molecular probe in the subject's brain compared to a control is indicative of the presence of the neurodegenerative disorder.

7. The method of claim 5, wherein the neurodegenerative disorder is Alzheimer's disease.

8. The method of claim 5, wherein the neurodegenerative disorder is Mild Cognitive Impairment.

9. The method of claim 5, wherein the neurodegenerative disorder is an early stage of Alzheimer's disease.

10. The method of claim 5, wherein the molecular probe is administered intravenously.

11. The method of claim 5, wherein the antibody is a monoclonal antibody.

12. A method of quantifying the pyro-Glu-(3-40/42)-Aβ load in a subject's brain comprising:
administering to the subject a molecular probe that includes:
(a) a detectable moiety, and
(b) an antibody or binding fragment thereof that specifically binds to an N-terminal epitope of pyro-Glu-(3-40/42)-Aβ that includes SEQ ID NO: 3, wherein the antibody or binding fragment thereof comprises at least one of (i) a heavy chain variable domain that includes the amino acid sequences of the three CDRs in SEQ ID NO: 13 and a light chain variable domain that includes the amino acid sequences of the three CDRs in SEQ ID NO: 14, (ii) a heavy chain variable domain that comprises the sequence of SEQ ID NO: 13, (iii) a light chain variable domain that comprises the sequence of SEQ ID NO: 14, or (iv) a heavy chain variable domain that comprises the sequence of SEQ ID NO: 13 and a light chain variable domain that comprises the sequence of SEQ ID NO: 14;
visualizing the molecular probe in the subject's brain with an in vivo imaging modality; and
correlating a distribution of the molecular probe in the subject's brain with the amount of pyro-Glu-(3-40/42)-Aβ in the subject's brain.

13. The method of claim 12, wherein the molecular probe is administered intravenously.

14. The method of claim 12, wherein the subject has or is at an elevated risk of Alzheimer's.

15. The method of claim 12, wherein the antibody is a monoclonal antibody.

* * * * *

SEQUENCE LISTING

<160> NUMBER OF SEQ ID NOS: 14

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 38
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 2

```
Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 3
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 3

Glu Phe Arg His Asp Ser
1               5

<210> SEQ ID NO 4
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 4

Glu Phe Arg His Asp Ser Gly
1               5

<210> SEQ ID NO 5
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 5

Glu Phe Arg His Asp Ser Gly Tyr
1               5

<210> SEQ ID NO 6
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 6

Glu Phe Arg His Asp Ser Gly Tyr Glu
1               5

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 7
```

```
Glu Phe Arg His Asp Ser Gly Tyr Glu Val
1               5                   10

<210> SEQ ID NO 8
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 8

Glu Phe Arg His Asp Ser Gly Tyr Glu Val His
1               5                   10

<210> SEQ ID NO 9
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 9

Glu Phe Arg His Asp Ser Gly Tyr Glu Val His His
1               5                   10

<210> SEQ ID NO 10
<211> LENGTH: 13
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 10

Glu Phe Arg His Asp Ser Gly Tyr Glu Val His His Gln
1               5                   10

<210> SEQ ID NO 11
<211> LENGTH: 14
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 11

Glu Phe Arg His Asp Ser Gly Tyr Glu Val His His Gln Lys
1               5                   10

<210> SEQ ID NO 12
<211> LENGTH: 15
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 12

Glu Phe Arg His Asp Ser Gly Tyr Glu Val His His Gln Lys Leu
1               5                   10                  15
```

```
<210> SEQ ID NO 13
<211> LENGTH: 143
<212> TYPE: PRT
<213> ORGANISM: Mus musculus

<400> SEQUENCE: 13

Met Lys Leu Trp Val Asn Trp Val Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Val Thr Ser Gly Phe Thr Phe
        35                  40                  45

Thr Glu Asn Tyr Met Ser Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Trp Asp Tyr Gly Ser Ser His Ala
        115                 120                 125

Met Asp Tyr Trp Gly Gln Gly Thr Ser Val Thr Val Ser Ser Ala
    130                 135                 140

<210> SEQ ID NO 14
<211> LENGTH: 126
<212> TYPE: PRT
<213> ORGANISM: Mus musculus

<400> SEQUENCE: 14

Met Val Ser Thr Ala Gln Phe Leu Val Phe Leu Leu Phe Trp Ile Pro
1               5                   10                  15

Ala Ser Arg Gly Asp Ile Leu Leu Thr Gln Ser Pro Ala Ile Leu Ser
            20                  25                  30

Val Ser Pro Gly Glu Arg Val Ser Phe Ser Cys Arg Ala Ser Gln Asn
        35                  40                  45

Ile Gly Thr Ser Met His Trp Phe Gln Gln Arg Thr Asn Gly Ser Pro
    50                  55                  60

Arg Leu Leu Ile Lys Tyr Ala Ser Glu Ser Val Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Gly Asp Ile Ala Asp Tyr Tyr Cys Gln Gln Ser Asn
            100                 105                 110

Ser Trp Pro Phe Thr Phe Gly Ser Gly Thr Lys Leu Glu Ile
        115                 120                 125
```